United States Patent [19]

Gluck et al.

[11] Patent Number: 4,747,403
[45] Date of Patent: May 31, 1988

[54] MULTI-FREQUENCY JET VENTILATION TECHNIQUE AND APPARATUS

[75] Inventors: Eric H. Gluck, West Hartford; Henry McDonald, S. Glastonbury; Jayant S. Sabnis, Glastonbury; Bernard C. Weinberg, West Hartford, all of Conn.

[73] Assignee: Advanced Pulmonary Technologies, Inc., Glastonbury, Conn.

[21] Appl. No.: 822,535

[22] Filed: Jan. 27, 1986

[51] Int. Cl.⁴ ............................................. A61M 16/00
[52] U.S. Cl. ............................ 128/204.21; 128/204.24; 128/204.25; 128/205.24
[58] Field of Search ................. 128/204.18, 204.21–25, 128/205.24, 207.17, 203.12, 203.14

[56] References Cited

U.S. PATENT DOCUMENTS

| | | | |
|---|---|---|---|
| 2,830,583 | 4/1958 | Finney, Jr. | 128/142 |
| 3,633,576 | 6/1972 | Gorsuch | 128/145.8 |
| 3,714,944 | 2/1973 | Price et al. | 128/203.12 |
| 3,741,208 | 6/1973 | Jonsson | 128/145.6 |
| 3,823,527 | 8/1970 | Foster | 128/145.6 |
| 3,840,006 | 10/1974 | Buck et al. | 128/145.8 |
| 3,863,630 | 2/1975 | Cavallo | 128/145.6 |
| 3,905,362 | 9/1975 | Eyrick et al. | 128/145.8 |
| 3,921,628 | 11/1975 | Smythe et al. | 128/145.6 |
| 3,976,064 | 8/1976 | Wood et al. | 128/145.8 |
| 4,011,866 | 3/1977 | Klein et al. | 128/145.8 |
| 4,033,343 | 7/1977 | Jones | 128/145.8 |
| 4,155,356 | 5/1979 | Venegas | 128/145.6 |
| 4,206,754 | 6/1980 | Cox et al. | 128/204.21 |
| 4,215,681 | 8/1980 | Zalkin et al. | 128/204.21 |
| 4,261,388 | 4/1981 | Glazner | 128/204.25 |
| 4,351,329 | 9/1982 | Ellostad et al. | 128/204.21 |
| 4,380,233 | 4/1983 | Caillot | 128/204.21 |
| 4,401,115 | 8/1983 | Monnier | 128/204.25 |
| 4,409,977 | 10/1983 | Bisera et al. | 128/205.15 |
| 4,450,838 | 5/1984 | Miodownik | 128/204.23 |
| 4,456,008 | 6/1984 | Clawson et al. | 128/204.25 |
| 4,463,756 | 8/1984 | Thuc | 128/204.21 |
| 4,471,773 | 9/1984 | Bunnell et al. | 128/204.21 |
| 4,481,944 | 11/1984 | Bunnell | 128/204.18 |
| 4,520,812 | 6/1985 | Freitag et al. | 128/204.25 |
| 4,538,604 | 9/1985 | Usry et al. | 128/204.25 |
| 4,612,929 | 9/1986 | Schubert | 128/204.25 |
| 4,617,924 | 10/1986 | Heim et al. | 128/204.25 |

FOREIGN PATENT DOCUMENTS

| | | | |
|---|---|---|---|
| 62653 | 6/1955 | France | 128/204.25 |
| 2144334 | 3/1985 | United Kingdom . | |

OTHER PUBLICATIONS

"Gas Washout and Pressure Waveform Characteristic of High-Frequency Oscillation", Perry et al., *Critical Care Med.*, vol. 12, No. 9, Sept, 1984, pp. 721–727.

"High Frequency Jet Ventilation Technical Implicators" Miodownik et al., *Critical Care Med.*, vol. 12, No. 9, Sept. 1984, pp. 718–720.

"Transport of Gases in High Frequency Ventilation", Jaeger et al., *Crit. Care Med.*, vol. 12, No. 9, Sept. 1984, pp. 708–710.

"Development of High Frequency Ventilation Techniques", Howland et al., *Crit. Care Med.*, vol. 12, No. 9, Sept. 1984, 705–707.

"Mechanisms Affective Gas Transport during High-Frequency Oscillation", Slutsky, *Crit. Care Med.*, vol. 12, No. 9, Sept. 1984, pp. 713–717.

*Primary Examiner*—Edward M. Coven
*Assistant Examiner*—K. M. Reichle
*Attorney, Agent, or Firm*—Chilton, Alix & Van Kirk

[57] ABSTRACT

Respiration therapy is accomplished by generating pulses of inhalation gas for delivery to a patient. The inhalation gas pulses may be generated by entraining humidified low pressure gas with pulses of high pressure entrainment gas. The pulses of entrainment gas may be of variable frequency, duration and duty cycle and are produced by modulating the flow of a highly pressured gas with a solenoid operated valve.

21 Claims, 4 Drawing Sheets

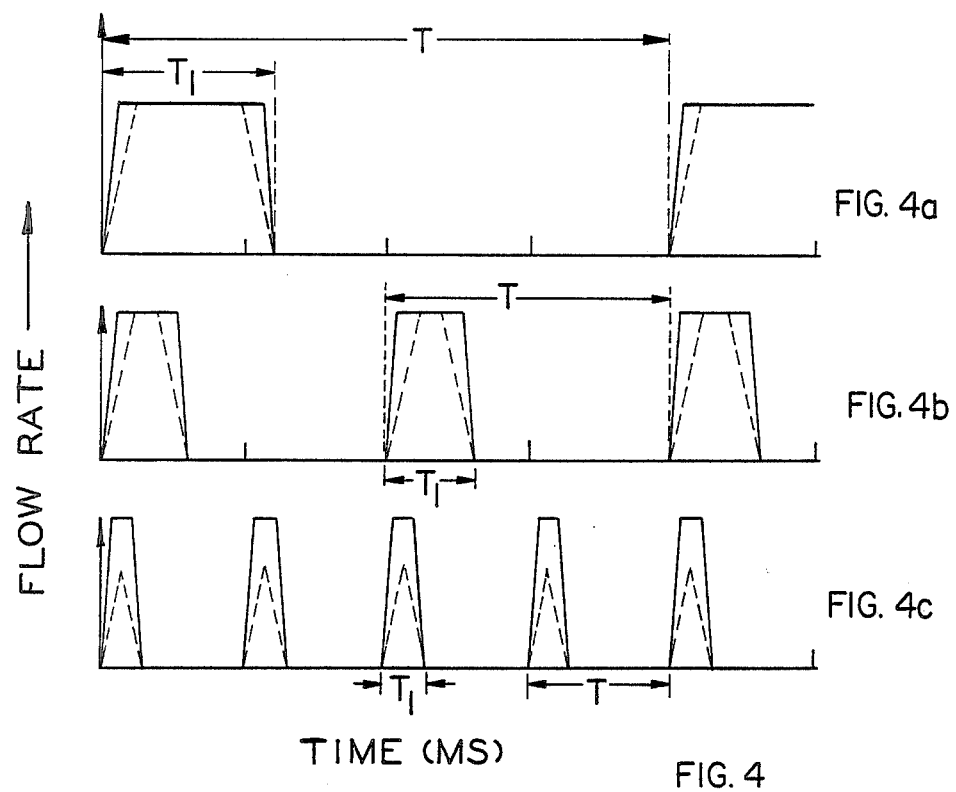
FIG. 4a
FIG. 4b
FIG. 4c
FIG. 4
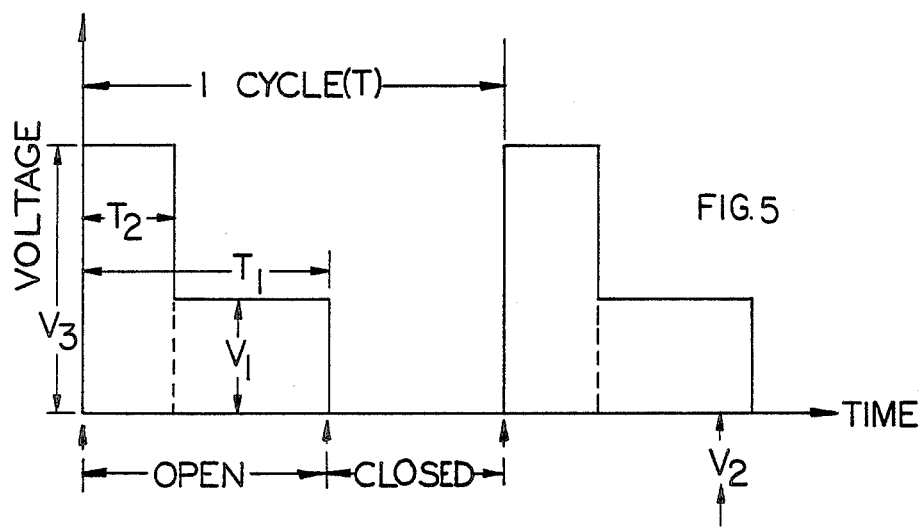
FIG. 5

MULTI-FREQUENCY JET VENTILATION TECHNIQUE AND APPARATUS

BACKGROUND OF THE INVENTION

1. Field of the Invention

This invention relates generally to ventilators for supplying gas to facilitate and support human respiration and particularly to ventilators which employ a high frequency jet of gas for respiratory therapy. More specifically, the present invention is directed to enhancing ventilation at supraphysiologic rates and especially to maximizing the tidal volume of gas delivered to a patient during respiration therapy while simultaneously minimizing patient discomfort and the possibility of causing or aggravating trauma. Accordingly, the general objects of the present invention are to provide novel and improved methods and apparatus of such character.

2. Description of the Prior Art

While not limited thereto in its utility, the present invention is particularly well suited to high frequency jet ventilation. The use of high frequency jet ventilation has proven to be quite beneficial in the treatment of certain respiratory conditions. In high frequency ventilation, rather than moving gas in bulk quantity into the gas exchanging areas of the lungs, ventilation is achieved by enhancing the mass transfer processes in the lungs through high frequency oscillation of the supplied gas. However, as the pulsation frequency of the gas delivered by a jet ventilator increases, supplying the necessary tidal volume of inhalation gas becomes more difficult and is limited by the response time of mechanisms employed for generating the gas pulses. In addition, the requirements of reliability, ease of maintenance and susceptibility to sterilization are important design considerations for a ventilator. Portability is a further desirable characteristic. Accordingly, the principal objectives of the present invention are to provide a new and improved ventilation technique and a multi-frequency jet ventilator which operates in accordance with this technique and is compact, relatively easy to maintain, capable of being easily sterilized and supplies a maximized tidal volume of ventilation gas flow over a wide range of frequencies and duty cycles.

SUMMARY OF THE INVENTION

Briefly stated, apparatus in accordance with a preferred embodiment of the invention comprises a ventilator system which includes a novel entrainment module. The entrainment module forms an entrainment chamber having an axis, an inhalation gas supply outlet, an inlet port for a bias flow of low pressure gas and a discharge or vent port. The inlet and discharge ports are axially spaced from the supply outlet and are located at generally diametrically opposite positions of the entrainment chamber. The low pressure gas, which will customarily be humidified, is continuously supplied to the inlet port from a first gas source to establish the bias flow during operation of the system. A nozzle extends into the entrainment chamber in a direction which is generally axially aligned with the inhalation gas supply outlet. The nozzle is in fluid communication with a source of relatively highly pressurized gas pulses and serves to inject a series of high velocity pressurized gas pulses into the entrainment chamber for traversal thereof in a generally axial direction toward the supply outlet. The gas pulses are injected from a zone generally located between the bias flow inlet and discharge ports, there being one high pressure pulse injected during the inspiratory phase of each cycle of the ventilator. A high velocity pulse from the nozzle entrains a relatively large amount of the low pressure gas from the bias flow in the entrainment chamber to produce an inhalation pulse which exits the chamber supply outlet. During each expiratory phase, between the injection of successive pulses from the nozzle, gases in the entrainment chamber, including $CO_2$ exhaled by the patient which flows into the chamber via the supply outlet, are vented through the discharge port.

The interior shape of the pulse injection nozzle is either convergent or convergent-divergent to increase the velocity of the gas comprising the pulses thus increasing the quantity of gas from the bias flow which is entrained. The entrainment module has a substantially T-shaped configuration, with the supply outlet being axially spaced from the nozzle opening and generally coaxial therewith, and contains no moving parts.

A conduit couples the source of high pressure ventilation gas to the nozzle. A valve is interposed in this conduit to selectively interrupt the flow of pressurized gas to generate the high pressure gas pulses. The valve is actuated by a solenoid which drives the valve from a closed to a fully open position. An electronic control circuit provides signals which control the operation of the solenoid. These commmand signals, in a preferred embodiment, have a frequency, pulse width and duty cycle which may be selected to provide the optimum ventilation program for the patient to be treated. The command signals have a generally stepped waveform which includes an initial overdrive voltage of predetermined duration. The overdrive voltage functions to reduce the time interval for the solenoid to change the state of the valve whereby the time required for the valve to switch from the fully closed to fully open condition is minimized.

The novel method of the present invention includes the steps of creating a humidified bias flow of gas and entraining gas from that bias flow to create a highly humidified inhalation gas. The entrainment consists of subjecting the bias flow to the effect of high velocity pulses of gas derived from a high pressure source of entrainment gas. The invention further contemplates the exercise of control over the entrainment gas to vary the frequency, duration and width of the gas pulses to satisfy the requirements of the treatment being performed.

BRIEF DESCRIPTION OF THE DRAWINGS

FIGS. 4a, 4b and 4c are graphical illustrations of gas pulse trains provided to the entrainment module of FIG. 2 in response to the control signals generated by the control module of FIG. 3; and FIG. 5 is a waveform diagram of a control voltage generated by the control module of FIG. 3.

DETAILED DESCRIPTION OF THE INVENTION

Figure 1:
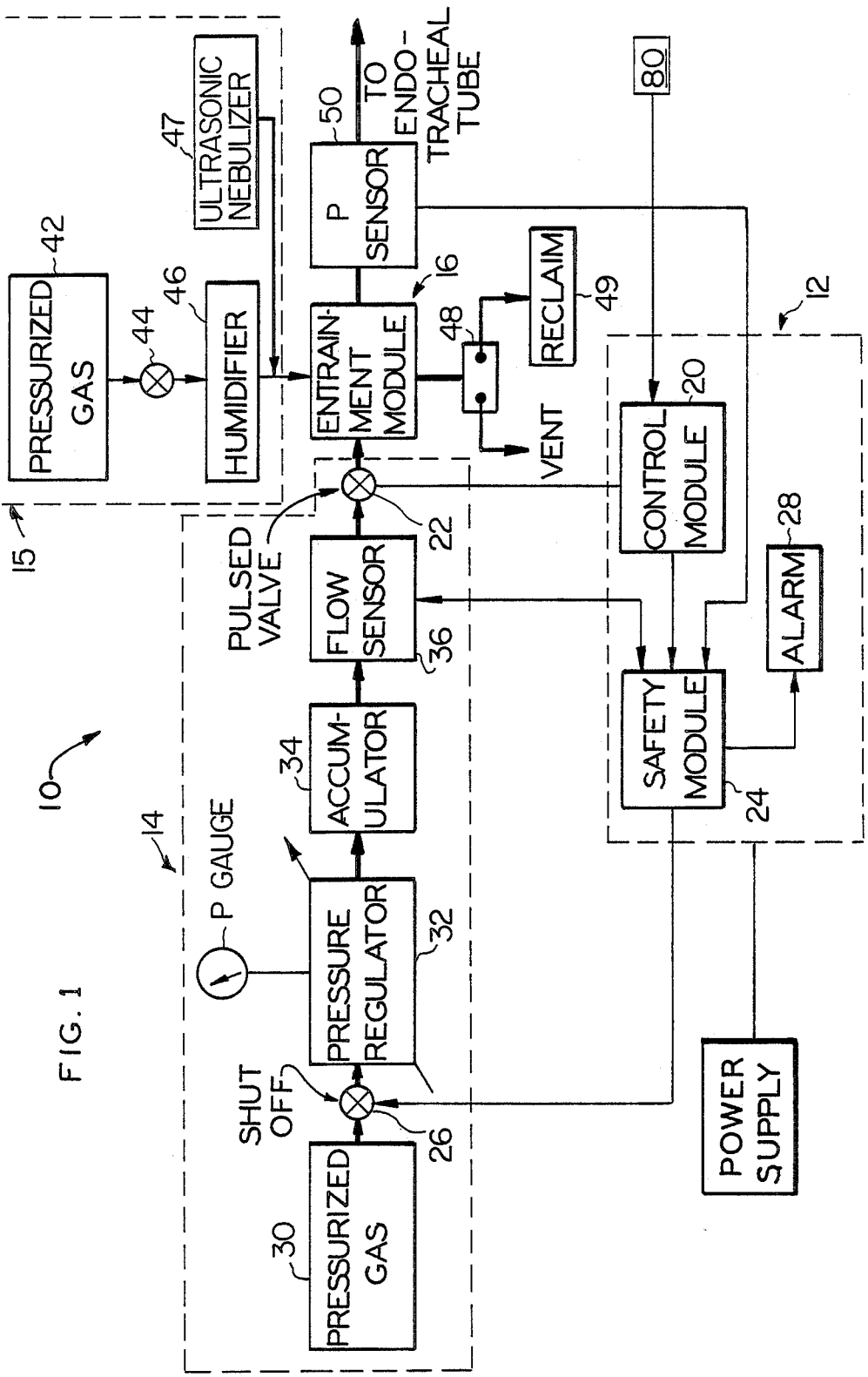
FIG. 1 is a functional block diagram of a multi-frequency jet ventilator in accordance with the present invention.

With reference to the drawing, wherein like numerals represent like parts throughout the several figures, a ventilator in accordance with one embodiment of the present invention is generally designated in FIG. 1 by the numeral 10. Ventilator 10 may be selectively employed at conventional ventilation frequencies or may be utilized as a high frequency jet ventilator. Ventilator 10 preferably has a range of operational frequencies of from 4 breaths/minute (1/15 Hz.) to 3000 breaths/minute (50 Hz) and an inspiratory time, i.e., a duty cycle, in the range of 5% to 95% as will be more fully described below. The ventilator 10 will supply respiratory gas to a patient via either a cuffed or uncuffed endotracheal tube (not illustrated) and is adaptable for ventilating with air, air/oxygen, helium/oxygen or any other suitable gas or combination of gases. Ventilator 10 has a compact, lightweight construction and may be either battery or line current powered.

Ventilator 10 is an integrated modular system which generally comprises a control unit 12, a high pressure gas supply unit 14, a low pressure gas supply unit 15 and an entrainment module 16. The control unit 12 comprises the electronic controls, safety system and the electrical power supply for the ventilator. The high pressure gas supply unit 14 comprises a source of high pressure gas, a gas pressure regulation system and a valve subassembly for producing controlled pulses of the gas derived from the high pressure source. The low pressure gas supply unit 15 comprises a source of low pressure gas and a humidification system for the gas. The entrainment module 16 produces, from the pulses of high pressure gas and the humidified low pressure gas, the required output of the ventilator. The gas flow lines are designated by heavy lines and the electrical interconnections are designated by thin lines in the drawing. The control unit 12 is connected to the supply unit 14 via conventional separable electrical connectors. The gas supply units 14 and 15 and entrainment module 16 are interconnected by standard flexible hoses. The above-mentioned modular units and their sub-units may be easily connected and disconnected. The modular construction thus facilitates maintenance of the ventilator and also provides a ventilator which, to the extent required, may be easily disinfected and sterilized as will be more fully apparent from the discussion below.

With reference to FIG. 1, the control unit 12 comprises an electronic control module 20 which generates control pulses for operating a solenoid actuated valve 22 in supply unit 14. The control module 20 also provides input signals to an electronic safety module 24. The safety module 24, in the manner to be described below, controls an electrically operated shutoff valve 26 in the primary, i.e., high pressure, gas supply line and is also connected to an alarm system 28.

A source of pressurized gas 30, which is typically in the form of plural tanks containing compressed dry air, oxygen/nitrogen, or oxygen/helium, is coupled via shutoff valve 26 and an adjustable pressure regulator 32 to an accumulator 34. The pressurized gas which appears at the output port of accumulator 34 has a regulated substantially constant pressure in the range of between 5 psi and 250 psi. The pressurized gas flows from the accumulator 34 via a flow sensor 36 and valve 22 to entrainment module 16. The flow sensor 36 provides an information bearing input signal to safety module 24 whereby the nature of the gas flow to the entrainment module 16 derived from high pressure source 30 may be continuously monitored to provide a means for actuating the alarm 28 in the event that the aforementioned gas flow is not within the selected and required operational limits of the ventilator. The alarm 28 is preferably both an audible and a visual alarm. The safety module 24, which is preferably a microprocessor, is programmed to monitor the operation of the ventilator, especially the primary gas flow to the entrainment module and the pressure downstream of the entrainment module, in order to determine whether the operating parameters are within pre-established ranges. Should a monitored parameter move into a range which is unsafe to the patient, module 24 will command the closing of shutoff valve 26.

A secondary pressurized gas source 42, within unit 15, is coupled via a shutoff valve 44 to a humidifier 46. The output of humidifier 46 is a bias flow of heated humidified gas which is continuously supplied to the entrainment module 40 at a relatively low pressure such as 5 psi. The secondary gas source 42 is typically in the form of one or more tanks containing the same gas as supplied by "high" pressure source 30. Humidifier 46 is preferably a cascade bubble humidifier and causes the bias flow to have approximately 100% relative humidity. In addition, an ultrasonic nebulizer 47 may be employed to introduce a vapor mist to the bias flow of humidified gas. The stream of humidified gas and vapor mist, which is flowing at low velocity, is entrained in module 16 by high velocity gas pulses, produced in the manner to be described below, to form an output gas stream. As noted above, the output stream is supplied to the patient via an endotracheal tube (not fully illustrated). The entrainment module 16 also functions to receive gases exhaled by the patient. Depending on the state of a two-way flow control valve 48, the exhaled gas is either vented to the ambient atmosphere or delivered to a reclaimation unit 49. Accordingly, during operation the vent port of the entrainment module will be maintained at a constant pressure which is equal to or less than atmospheric. A pressure sensor 50 may be interposed in the gas path which extends from the entrainment module to the endotracheal tube for sensing the pressure immediately upstream of the endotracheal tube and providing a corresponding input signal to the safety module 24 for insuring safe operation of the ventilator.

Figure 2:
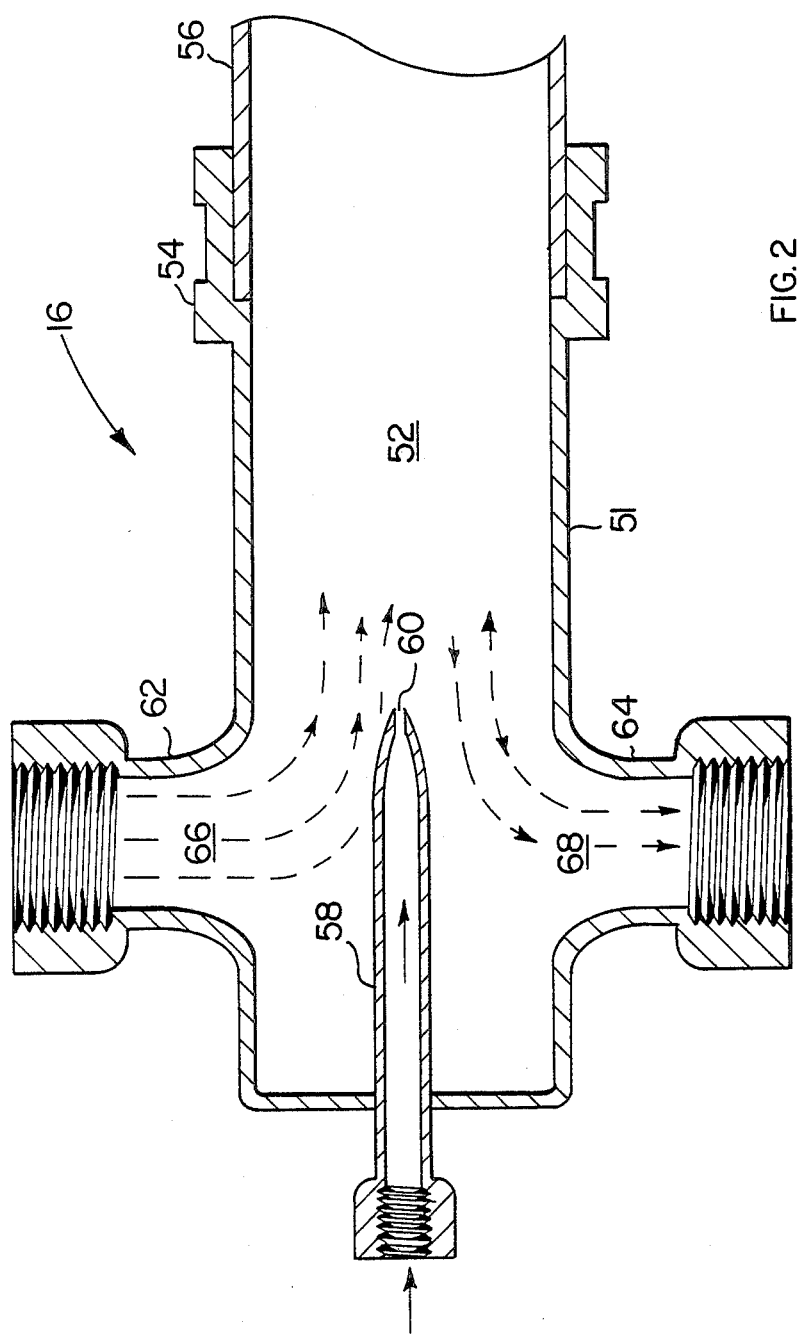
FIG. 2 is an enlarged fragmentary sectional view of a preferred embodiment of the entrainment module of the multi-frequency jet ventilator of FIG. 1.

With reference to FIG. 2, the entrainment module 16 comprises a housing 51 which interiorly forms an entrainment chamber 52. Housing 51 is a generally T-shaped cylindrical member which has an open output end. A fitting 54 at the output end fluidically couples chamber 52 to a conduit 56 which leads to or comprises the end of the endotracheal tube. Gas pulses, produced by modulating the gas exiting accumulator 34 by means of valve 22, are injected into the entrainment chamber 52 through a nozzle 58. Nozzle 58 is a convergent or convergent-divergent nozzle and thus the velocity of the gas downstream of the nozzle throat is high. Nozzle 58 extends axially into chamber 52 through an end wall of the housing 51 along the central axis of the chamber. Nozzle 58 is aerodynamically shaped to enhance entrainment efficiency by directing the low pressure bias flow in the downstream direction in chamber 52. Nozzle 58 thus preferably has a forwardly tapering convergent external profile as shown, i.e., nozzle 58 is externally shaped to smoothly diverge in the upstream direction from the discharge end thereof. An inlet leg 62 and an outlet leg 64 protrude radially at diametrically opposite locations of housing 51. Legs 62 and 64 are substantially identical and are equidistant from the centrally disposed nozzle 58. Inlet leg 62 functions as a connector structure for coupling to a conduit for supplying the low velocity bias stream of humidified gas to the entrainment chamber 52 via port 66 as illustrated by the arrows in FIG. 2. The humidified gas is continuously supplied to the entrainment chamber. During an inspiratory phase of the ventilation cycle, humidified gas is entrained by a high velocity gas pulse injected into chamber 52 via the nozzle 58 and propelled axially through the chamber to conduit 56 and thence to the patient via the endotracheal tube. The ventilating gas pulses delivered to the patient will be comprised primarily of humidified gas supplied via inlet leg 62, the humidified gas being entrained by the pulses of dry gas supplied via nozzle 58. Accordingly, the patient will receive gas having the highest possible relative humidity.

During the expiratory phase of the ventilation cycle, the gas exhaled by the patient returns via conduit 56 to the entrainment chamber 52. The exhaled gas is entrained by the low velocity bias flow and is thus discharged through discharge or vent port 68 which leads to outlet leg 64. Leg 64 is coupled to a conduit for conducting the exhaled gas and excess humidified gas to valve 48. The expired carbon dioxide from the patient is discharged through port 68 in part due to the driving force of the bias flow of humidified gas which prevents the exhaled gases from entering port 66 and thus a vent or discharge control valve is not required.

The entrainment of the humidified gas by the high velocity pulses or slugs of primary gas is facilitated by the convergent exterior shape of nozzle 58 which, as mentioned above, functions as a flow control surface. The entrainment of the humidified gas is improved by the placement of the outlet 60 of nozzle 58 at an axial location of the chamber which is proximate the downstream axial terminus of the inlet port 66. Consequently, the high velocity pulse is injected into the chamber at a location slightly downstream from the entry of the humidified gas. As should now be obvious, the continuous supply of the low pressure humidified secondary gas functions to alternately supply humidified gas for entrainment and to remove the expired carbon dioxide from the ventilator unit without the use of any mechanical valves which would otherwise tend to deteriorate the entrainment effects and, thus, would result in lower tidal volumes.

A low compliant tube connects nozzle 58 to the solenoid actuated control valve 22. Valve 22 is a bi-state valve having an open and closed position. The command signals generated by control module 20 and applied to the solenoid of valve 22 determine the frequency and duration of the gas pulses delivered to nozzle 58. Thus, valve 22 is cyclically opened and closed for selected time intervals to interrupt the flow of pressurized gas to nozzle 58 to thereby produce the desired gas pulse train characteristics to provide optimum treatment for the patient.

The characteristics of the train of pressurized gas pulses produced by valve 22 may best be appreciated by reference to FIGS. 4a, 4b and 4c. The horizontal axes represent the time in milliseconds and the vertical axes represent the flow rate of the high velocity ventilation gas exiting nozzle 58. The letter T represents the time of one ventilation cycle, i.e., the time of a inspiratory phase plus the time of a following expiratory phase. The symbol $t_1$ represents the time interval during which valve 22 is open. For each of the graphs of FIG. 4, the time interval in which valve 22 is opened, i.e., the inspiratory time, is 30 percent of the ventilation cycle T. The graph of FIG. 4a represents the pulse train characteristics when valve 22 is opened and closed at a 5 Hz. frequency. Graph 4b represents the pulse characteristics when valve 22 is opened and closed at a 10 Hz. frequency. FIG. 4c represents the pulse characteristics when valve 22 is opened and closed at a 20 Hz. frequency.

The volume of gas supplied by the valve per breath is equal to the area under the flow rate-time curve of the graphs of FIG. 4. The solid lines represent the flow characteristics for ventilator 10. The broken lines represent the flow characteristics for a ventilator which does not incorporate a feature for reducing the time required for the valve to change states in accordance with the present invention. It will be appreciated that the depicted curves have a trapezoidal shape rather than a square wave shape due to the incremental time interval required for valve 22 to change from one state to another, i.e., from a fully closed state to a fully open state and vice versa. In the prior art, at high pulse frequencies there was insufficient time for the valve to open completely before receipt of a "close" command. Accordingly, the triangular flow pattern indicated by the broken lines of FIG. 4c resulted. A flow pattern as represented by the broken line showing of FIG. 4c leads to a drastic reduction in the tidal volume, i.e., the volume of gas supplied to the patient, during the inspiratory phase. Consequently, in order that sufficient tidal volumes be supplied at high ventilation frequencies, the valve must be caused to react quickly to "open" commands and should remain open for a significant portion of the inspiratory phase.

Figure 3:
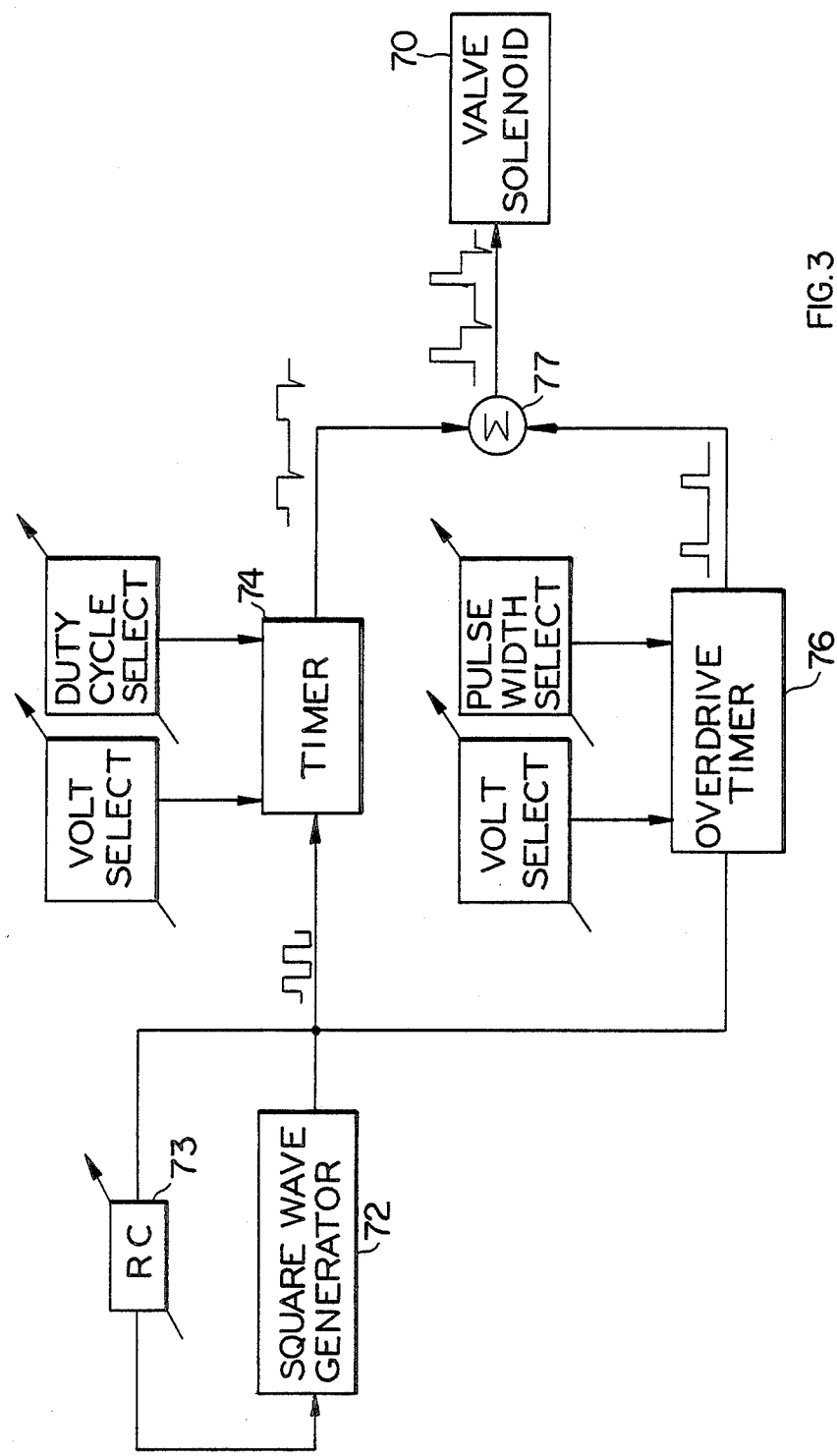
FIG. 3 is a functional block diagram of the control module of the multi-frequency jet ventilator of FIG. 1.

With reference to FIG. 3, valve 22 is opened and closed by means of solenoid 70 which is responsive to command signals generated by the control module 20. Control module 20 includes a square wave generator 72. A resistance capacitance network 73 is adjustable in the conventional manner to vary the time constant of and thus the output frequency of square wave generator 72. The square wave output signal of generator 72 is applied to a timer circuit 74. Referring jointly to FIGS. 3 and 5, an adjustable voltage magnitude selection circuit and an adjustable duty cycle selection circuit are coupled to timer 74 to cause the timer to provide an output waveform having a selected amplitude (voltage $V_1$), pulse width (time $t_1$) and frequency f. Voltage $V_1$ is selected to be the minimum solenoid holding voltage required to sustain valve 22 in the opened position. This voltage is typically lower than the voltage necessary to cause the solenoid to open the valve. Use of a low voltage to maintain the valve open reduces the closing time for the valve. The closing time is further reduced by a short duration large negative voltage spike $-V_2$ which is generated at the end of the inspiratory phase of the cycle upon removal of the timer 74 output voltage from the valve solenoid. Time $t_1$ is selected to provide the optimum inspiratory time per ventilation cycle. Frequency f is selected to provide the optimum ventilation frequency in accordance with the condition of the patient. The square wave from circuit 72 is also applied to an overdrive timer circuit 76. The overdrive timer circuit is also adjustable to generate a second waveform having a second amplitude (voltage $V_3-V_1$) and second pulse width (time $t_2$) with the same frequency f as and in phase with the waveform provided by timer 74. Voltage $V_3-V_1$ and time $t_2$ are selected to reduce the valve opening time as detailed hereinafter. The two waveforms are combined, as represented schematically by summing circuit 77, and applied to solenoid 70. The waveform applied to solenoid 70 is illustrated in FIG. 5. The period of one opening and closing phase or cycle of valve 22, and hence the ventilation cycle, is given by time T. By applying the overdrive voltage $V_3-V_1$ to the solenoid, the overdrive voltage having an amplitude which is at least three times as great as the holding voltage $V_1$, a greater electromagnetic force is generated, and the opening time of the valve is significantly reduced. Thus, the tidal volumes produced by the ventilator at high frequencies is not substantially reduced by the time required for the valve to change its state. As noted above, in the graphs of FIG. 4 the broken lines illustrate generally the pulse characteristics without application of the overdrive voltage to the solenoid and the solid lines represent the pulse characteristics of the ventilator when the foregoing described overdrive voltage is applied from the control module.

It will be appreciated that the ventilator 10 is operated by selecting an optimum frequency and duty cycle, i.e., the ratio of inspiration time to ventilation cycle time, for the condition of the patient. The tidal volume of ventilation gas supplied to the patient is a function of pulse frequency and duration as well as gas pressure. Pressure regulator 32 regulates the pressure by conventional means. The control module functions to electronically control valve 22 to provide the optimum ventilation characteristics. The latter characteristics may change over the treatment period and the ventilator of the present invention is capable of manual or automatic readjustment in accordance with varying patient requirements. In actual practice, the control and safety modules may be a single subassembly including a programmable microprocessor and the operational mode may be entered from a keyboard and/or selected from preprogrammed data. Since variation of the ventilation parameters can be accomplished without disconnecting the patient from the ventilator, trauma is avoided that could otherwise occur. It should be appreciated that since the ventilator is of modular construction, sterilization and maintenance of the unit can be relatively easily achieved. The entrainment module 16 has no moving components and thus may be easily disconnected from the ventilator for sterilization and/or replacement.

The present invention has the flexibility, particularly operational parameters which are adjustable over broad ranges, which enables its use in a synchronous intermittent mandatory ventilation (IMV) mode. The IMV mode will be selected, via the microprocessor based control module 20, when it is desired to attempt to wean a patient from the ventilator. In the IMV mode a pulse, at a frequency less than the normal breathing rate, will be provided by a clock in the microprocessor to trigger the generation of command signals for the valve 22 solenoid. A sensor 80, which could be a pressure sensor in the endotracheal tube, will sense spontaneous breathing by the patient and provide signals commensurate therewith which are inputted to control module 20. The valve 22 will open at the selected frequency except each time spontaneous exhalation is sensed, in which case the opening of the valve will be delayed until the end of exhalation and the clock will be reset to zero.

The present invention may also, with the removal of the entrainment module 16 and low pressure gas supply unit 15, be employed in the case of a transcutaneous cricothyroidalostomy. In emergency situations, for example under battlefield conditions or in the case of medical technicians at the scene of an accident, a patient experiencing breathing difficulty cannot be provided with an endotracheal tube. That is, the proper insertion of an endotracheal tube may require as long as one-half hour, requires good lighting and requires a highly trained medical professional. The present invention, with the entrainment module removed but a nozzle similar to nozzle 58 retained, can be utilized by medical technicians in the following manner. A needle with associated catheter will be inserted into the trachea, the needle will then be withdrawn and the nozzle then inserted into the trachea via the catheter. Jet ventilation may then be started with exhalation being via the patient's mouth and/or nose.

While preferred embodiments of the invention have been set forth for purposes of illustration, the foregoing description should not be deemed a limitation of the invention disclosed herein. Accordingly, various modifications, adaptations and alternatives may occur to one skilled in the art without departing from the spirit and the scope of the present invention.

What is claimed is:

1. A variable frequency jet ventilator system comprising:
    entrainment module means for defining an entrainment chamber having an axis and a supply outlet which is coaxial with said chamber, said entrainment module means further defining an inlet port and a constantly open vent port for said entrainment chamber, said inlet and vent ports being in uninterrupted fluid communication via said entrainment chamber whereby gas entering said entrainment chamber through said inlet port may continuously flow through said vent port, each of said ports having an axis and upstream and downstream ends, said inlet port and said vent port being generally axially aligned;
    means connected to the upstream end of said inlet port for continuously supplying humidified gas to said entrainment chamber via said inlet port to thereby establish a bias flow across said entrainment chamber between said inlet and vent ports;
    means for generating pulses of gas;
    means for controlling said pulse generating means to vary the frequency of generation of the gas pulses;
    nozzle means for imparting a high velocity to gas pulses, said nozzle means having a discharge end which opens into said entrainment chamber, said nozzle means being fluidically coupled to said pulse generating means to receive the pulses of gas whereby high velocity gas pulses are discharged into said entrainment chamber, said nozzle means being oriented to cause the discharged gas pulses to be directed along said entrainment chamber axis toward said supply outlet, said nozzle means being positioned such that high velocity gas pulses discharged from said nozzle means will entrain humidified gas from the bias flow to produce humidified gas pulses which exit said supply outlet; and
    means coupled to said entrainment chamber supply outlet for delivering the humidified gas pulses to a patient's respiratory system.

2. The ventilator system of claim 1 wherein said nozzle means has an axis which is coaxial with said discharge end and said chamber and protrudes into said chamber so as to extend at least part way into the bias flow.

3. The ventilator system of claim 2 wherein the entrainment module means has a generally T-shaped configuration, respective arm portions of said T-shaped configuration defining said inlet and vent ports whereby said inlet and vent ports are coaxial, the stem of said T-shaped configuration being coaxial with said chamber axis whereby said inlet and vent ports are oriented generally transversely with respect to said chamber axis.

4. The ventilator system of claim 3 wherein said nozzle means is exteriorly configured to at least in part direct the bias flow in the direction of said entrainment chamber supply outlet.

5. The ventilator system of claim 1 wherein said pulse generating means comprises:
   a source of highly pressurized gas;
   a conduit providing fluid communication between said source of highly pressurized gas and said nozzle means; and
   normally closed controllable valve means interposed in said conduit to selectively interrupt the flow of pressurized gas through said conduit, said valve means being connected to said controlling means whereby said valve means is responsive to said controlling means.

6. The ventilator system of claim 5 wherein said valve means comprises a solenoid actuated valve and wherein said controlling means comprises electronic control means for generating a variable frequency electrical signal for energizing the solenoid of said valve to cause opening of said valve.

7. The ventilator system of claim 6 wherein said nozzle means has an axis which is coaxial with said discharge end and said chamber and protrudes into said chamber so as to extend at least part way into the bias flow.

8. The ventilator system of claim 7 wherein the entrainment module means has a generally T-shaped configuration, respective arm portions of said T-shaped configuration defining said inlet and vent ports whereby said inlet and vent ports are coaxial, the stem of said T-shaped configuration being coaxial with said chamber axis whereby said inlet and vent ports are oriented generally transversely with respect to said chamber axis.

9. The ventilator system of claim 8 wherein said electronic control means comprises means for generating solenoid control voltage pulses having first and second magnitude levels, the second voltage level being sufficient to cause current flow through said solenoid adequate to hold said valve in the open state but insufficient to open said valve, the first voltage level being greater than the second voltage level and causing sufficient current flow through said solenoid to actuate said valve from the closed state to the open state.

10. The ventilator of claim 9 wherein said electronic control means includes means for varying the width and duty cycle of said solenoid control voltage pulses and said pulses have a stepped waveform with a substantially instantaneous rise time.

11. The ventilator system of claim 10 wherein said nozzle means is exteriorly configured to at least in part direct the bias flow in the direction of said entrainment chamber supply outlet.

12. The ventilator system of claim 6 wherein said electronic control means comprises means for generating solenoid control voltage pulses having first and second magnitude levels, the second voltage level being sufficient to cause current flow through said solenoid adequate to hold said valve in the open state but insufficient to open said valve, the first voltage level being greater than the second voltage level and causing sufficient current flow through said solenoid to actuate said valve from the closed state to the open state.

13. The ventilator of claim 12 wherein said electronic control means includes means for varying the width and duty cycle of said solenoid control voltage pulses.

14. The ventilator system of claim 13 wherein said nozzle means protrudes into said chamber so as to extend at least part way into the bias flow and is externally configured to at least in part direct the bias flow in the direction of said entrainment module means supply outlet.

15. The ventilator system of claim 1 wherein said nozzle means protrudes into said chamber so as to extend at least part way into the bias flow and is externally configured to at least in part direct the bias flow in the direction of said entrainment module means supply outlet.

16. The ventilator system of claim 1 wherein said means for supplying humidified gas includes:
   a source of pressurized ventilation gas;
   means coupling said source of ventilation gas to said entrainment chamber inlet port; and
   means disposed in said coupling means for humidifying the gas discharged from said source, said humidfying means being positioned upstream of said entrainment module means inlet port in the direction of flow of ventilating gas through said coupling means.

17. The ventilator system of claim 16 wherein said humidifying means comprises:
   a first humidifier; and
   ultrasonic nebulizer means located downstream of said first humidifier in the direction of gas flow through said coupling means for introducing a vapor mist into the humidified gas from said first humidifier.

18. A variable frequency jet ventilation system comprising:
   means for generating gas pulses, said gas pulse generating means including:
      a source of pressurized gas, said gas source having a discharge port;
      conduit means having first and second ends, said conduit means being coupled at a first end thereof to said discharge port;
      normally closed valve means interposed in said conduit means to selectively interrupt the flow of pressurized gas from said source through said conduit means, said valve means comprising a solenoid actuated valve; and
      means for generating control voltage pulses for said valve means solenoid operated valve, said control voltage pulses each having at least initial and second magnitude levels, said second voltage level being sufficient to cause current flow through the solenoid of the valve adequate to hold the valve in the open state but insufficient to open the valve, said initial voltage level being greater than said second voltage level and causing sufficient current flow through the solenoid of the valve to actuate the valve from the closed state to the open state;

means defining an entrainment chamber, said entrainment chamber having a supply outlet at one end thereof, said supply outlet having an axis;

nozzle means for imparting high velocity to gas pulses delivered thereto, said nozzle means being in fluid communication with said gas pulse generating means via the second end of said conduit means and having an open discharge end which extends into said entrainment chamber whereby the generated gas pulses are accelerated injected into said chamber, said nozzle means having an axis and which is generally coaxial with said discharge end and said entrainment chamber supply outlet whereby gas pulses injected into said entrainment chamber from said nozzle means discharge end are directed toward said supply outlet, said nozzle means being at least in part externally shaped to smoothly diverge in the upstream direction from the discharge end thereof;

means for establishing a stream of gas across said entrainment chamber, the established gas stream being directed to at least in part intersect the axis of said nozzle means and supply outlet, the gas stream establishing means being located and oriented such that gas pulses from said nozzle means will entrain gas from the gas stream and carry the entrained gas through said supply outlet;

means for constantly venting said entrainment chamber, said venting means being positioned to receive the gas stream; and means coupled to said entrainment chamber defining means supply outlet for delivering the gas pulses with entrained gas from the stream to the respiratory system of a patient.

19. The ventilation system of claim 18 wherein said stream establishing means provides a continuous flow of humidified gas.

20. The ventilation system of claim 19 wherein the flow of humidified gas at least in part impinges upon said divergent part of said nozzle means whereby a portion of the flow is redirected generally in the direction of said entrainment chamber supply outlet.

21. The ventilation system of claim 18 wherein the gas stream at least in part impinges upon said divergent part of said nozzle means whereby a portion of the stream is redirected generally in the direction of said entrainment chamber supply outlet.

* * * * *